United States Patent [19]
Haynie

[11] Patent Number: 5,240,415
[45] Date of Patent: Aug. 31, 1993

[54] DENTAL BLEACH SYSTEM HAVING SEPARATELY COMPARTMENTED FUMED SILICA AND HYDROGEN PEROXIDE AND METHOD OF USING

[76] Inventor: Michel B. Haynie, 1259 E. 8320 South, Sandy, Utah 84094

[21] Appl. No.: 922,319

[22] Filed: Jul. 30, 1992

Related U.S. Application Data

[63] Continuation-in-part of Ser. No. 534,715, Jun. 7, 1990, abandoned.

[51] Int. Cl.⁵ .............................................. A61C 15/00
[52] U.S. Cl. ..................................... 433/216; 433/217.1; 433/229; 206/63.5; 424/53
[58] Field of Search .................... 433/216, 217.1, 229; 206/63.5; 424/53, 49

[56] References Cited

U.S. PATENT DOCUMENTS

| | | | |
|---|---|---|---|
| 1,826,809 | 10/1931 | Metz | 206/532 |
| 3,756,386 | 9/1973 | Marckardt | 206/63.5 X |
| 4,060,600 | 11/1977 | Vit | 433/216 X |
| 4,141,144 | 2/1979 | Lustgarten | 433/217.1 |
| 4,512,743 | 4/1985 | Santucci et al. | 433/217.1 |
| 4,661,070 | 4/1987 | Friedman | 433/229 X |
| 4,687,663 | 8/1987 | Schaeffer | 424/53 X |
| 4,788,052 | 11/1988 | Ng et al. | 424/616 X |
| 4,839,156 | 6/1989 | Ng et al. | 424/53 |
| 4,849,213 | 7/1989 | Schaeffer | 424/53 |
| 4,852,742 | 8/1989 | Scuorzo | 206/63.5 X |
| 5,032,178 | 7/1991 | Cornell | 433/216 X |

*Primary Examiner*—John J. Wilson
*Assistant Examiner*—Jeffrey A. Smith
*Attorney, Agent, or Firm*—J. Winslow Young

[57] ABSTRACT

A dental bleach system and method whereby fumed silica is used as a base for forming a paste with a solution of hydrogen peroxide, the paste acting as a nonreactive carrier to control the delivery of the hydrogen peroxide solution to the dental surface. The fumed silica is provided as a predetermined quantity in a mixing chamber while the hydrogen peroxide solution is provided as a premeasured volume in an ampule. Both items are made available to the dental care professional in a single patient use kit.

12 Claims, 1 Drawing Sheet

DENTAL BLEACH SYSTEM HAVING SEPARATELY COMPARTMENTED FUMED SILICA AND HYDROGEN PEROXIDE AND METHOD OF USING

RELATED APPLICATIONS

This application is a continuation-in-part patent application of my copending patent application Ser. No. 07/534,715 filed 7 Jun. 1990 for DENTAL BLEACH AND METHOD (now abandoned).

BACKGROUND

1. Field of the Invention

This invention relates to dental bleaches and, more particularly, to a novel dental bleach and method for use by a dental professional to remove stains from teeth whereby the dental professional is provided with a container of fumed silica and a container of hydrogen peroxide that can be mixed directly into the fumed silica to form a paste that is easier to use and safer to handle.

2. The Prior Art

Discolorations of the dentition are traditionally classified into two main categories, extrinsic and intrinsic. Extrinsic stains result from the deposition of a film, pigment or calculus on the teeth. The familiar extrinsic discolorations generally result from the superficial staining of tooth surfaces. Coffee, tea, artificial food colorations, grapes, berries, and the smoking or chewing of tobacco are the usual causatives. The intensity of these stains may be worsened if there are enamel defects such as pits, cracks, grooves, when the dentin is exposed, or when recession has bared the root surface. These irregularities allow the stain to penetrate the tooth to a depth that makes removal of the stain extremely difficult or virtually impossible.

Intrinsic discolorations result from several causes which have either an endogenous or exogenous origin and which may occur during or after odontogenesis. During odontogenesis teeth may become discolored from changes in the quality or quantity of enamel or dentine, or from incorporation of discoloring agents into the hard tissues. Post-eruption discolorations occur when discoloring agents enter the dental hard tissues and may originate from the pulp cavity or tooth surface.

Intrinsic discolorations that occur during odontogenesis may result from a number of causes including inherited metabolic disorders such as ochronosis, also known as alkaptonuria or phenylketonuria, which is characterized by incomplete oxidation of tyrosine and phenylanine causing a buildup of homogenestic acid. This buildup may result in a dark brown discoloration of the permanent teeth.

Porphyria is a rare disorder of porphyrin metabolism and is usually congenital but can be acquired later in life. The hematoporphyrin pigment caused a characteristic reddish-brown discoloration of the teeth, called "erythrodontia" and is dispersed throughout the enamel, dentine and cementum.

Dental fluorosis is an enamel hypoplasia resulting from excessive ingestion of fluoride during the critical stages of dental development. The degree of fluorosis is directly proportional to the amount of fluoride absorbed. A brown stain of extrinsic origin is acquired of few years after the affected tooth as erupted into the oral cavity.

Tetracycline affects both the permanent teeth as well as the deciduous teeth because of its ability to cross the placental barrier. During mineralization tetracycline binds to the calcium to form a calcium-phosphate-tetracycline complex. The severity of the discoloration is related to the dose, duration, timing, and type of drug administered.

Intrinsic discoloration after odontogenesis results from several causes including trauma, aging, metals, dental materials, or foods and beverages. Trauma can cause hemorrhage in the dental pulp which ma result in the diffusion of blood pigments into the dental tubules. Aging, secondary and tertiary (atypical) dentine formation and pulp stones can also cause the tooth to appear a yellowish-brown color.

By direct contact and oxidation or by precipitation from the blood stream or saliva, metals may deposit in the dentine, cementum or enamel. The most common cause of metallic staining is corrosion products from amalgam restorations. Dental materials containing therapeutic agents such as polyantibiotic pastes, oil of cloves, creosote and the like can also discolor the dentition.

One of the commonly practiced techniques for removing discolorations, both extrinsic and intrinsic, is the practice of external bleaching. Hydrogen peroxide has been known for years as a dental bleaching agent although its cleansing action affects discoloring agents located within five to seven microns from the enamel surface. This is explained by the high inorganic content and limited permeability of the enamel. One report suggests that the improvement of esthetics in cases of tetracycline and similar type stainings using hydrogen peroxide is attributed more to the alteration of the light refraction of the surface enamel than to the removal of the discoloring agents and continues on to suggest that the results are only temporary.

Several techniques exist for the application of hydrogen peroxide as a bleaching agent. The major point of difference in these techniques are the temperature to which the tooth is heated and the duration of that heating so that there appears to be no apparent consensus established for the time and temperature. Apparently, the pain threshold of the patient to the treatment is the guideline so that these parameters will be established by the patient reaction which can be altered by the psychological state of the patient.

The basic prior art technique for bleaching a tooth is to carefully shield the patient's surrounding gum tissue using a tight fitting rubber dam along with petrolatum or cocoa butter between the dam and the soft tissue. The tooth surface is then treated with a flour of pumice and etched with thirty-seven percent phosphoric acid for one minute after which it is washed and dried. The enamel surfaces are then treated by applying cotton gauze or the equivalent saturated with thirty percent hydrogen peroxide and a low heat treatment is applied. One technique for heating is through an exothermic chemical reaction caused by mixing calcium carbonate with the hydrogen peroxide. Other heat sources can also be used, such as a heating lamp or a heated metal instrument applied to the tooth. The tooth is then washed thoroughly, dried and sealed with a sealing agent. At all times, great care is taken to protect both the patient and the dental team from the liquid hydrogen peroxide.

A number of publications discuss various aspects of the foregoing, including by way of example:

"Bleaching," by Ronald A. Feinman, DMD, *CDA Journal*, April 1987, pages 10-13.

"Chemical agents for removing intrinsic stains from vital teeth. I. Technique development," by Susan A. McEvoy, DMD, MS, *Quintessence International*, Vol. 20, No. 5, 1989, pages 323-328.

"Chemical agents for removing intrinsic stains from vital teeth. II. Current techniques and their clinical application," by Susan A. McEvoy, DMD, MS, *Quintessence International*, Vol. 20, No. 6, 1989, pages 379-384.

"Bleaching Stains Related to Trauma or Periapical Inflammation," by Susan A. McEvoy, DMD, MS, *The Compendium of Continuing Education*, Vol. VII, No. 6, June 1986, pages 420-428.

"Bleaching Vital Teeth: A Review and Clinical Study," by Dan Nathanson, DMD, MSD and Cesar Parra, DDS, *Compend Contin Educ Dent.*, Vol. VIII, No. 7 pages 490-497.

"Anterior composite resins and veneers: treatment planning, preparation, and finishing," by Alan R. Weinstein, DDS, *JADA* (Special Issue), September 1988, pages 38E-45E.

"Bleaching teeth: new materials-new role," by Ronald E. Goldstein, DDS, *JADA* (Special Issue), December, 1987, pages 44E-52E.

"An In Vitro Comparison of Different Bleaching Agents in the Discolored Tooth," by Stewart Ho, DMD and Albert C. Goerig, DDS, MS, FICD, *Journal of Endodontics*, Vol. 15, No. 3, March 1989, pages 106-111.

"Bleaching Procedures for Teeth with Vital and Nonvital Pulps," by Richard E. Walton, *Current Treatment in Dental Practice*, N. Levine (ed.), Philadelphia: W. B. Saunders, 1986, page 202.

"A method for bleaching discolored vital teeth," by Edward J. Swift, Jr., DMD, *Quintessence International*, Vol. 19, No. 9, 1988, pages 607-612.

"The Role of Bleaching in Esthetics," by Donald Arens, DDS, MSD, *Dental Clinics of North America*, Vol. 33, No.2, April 1989, pages 319-336.

"The Etiology and Treatment of Intrinsic Discolourations," by P. A. Hayes, DMD, C. Full, B.S., DDS, MS and J. Pinkham, BS, DDS, MS, *J. Canadian Dental Assoc.*, Vol. 52, No. 3, March 1986, pages 217-220.

Hydrogen peroxide has long been recognized for its effectiveness in curative and/or prophylactic treatments with respect to caries, dental plaque, gingivitis, periodontia, mouth odor, tooth stains, recurrent aphthous ulcers, denture irritations, orthodontic appliance lesions, post extraction and postperiodontal surgery, traumatic oral lesions and mucosal infections, herpetic stomatitis, and the like. Peroxide-containing agents in the oral cavity exert a chemomethanical action generating thousands of tiny oxygen bubbles produced by interaction with tissue and salivary enzymes.

However, it is well known that hydrogen peroxide in oral compositions is unstable in storage due to its incompatibility with and/or interaction with other common ingredients in the composition. Numerous attempts have been made to overcome this problem and to thereby provide a suitable dental product having hydrogen peroxide as an active ingredient without its having lost its inherent, oxygen-producing capability.

Sompayrac (U.S. Pat. No. 4,226,851) discloses a stable dental hygiene composition including hydrogen peroxide and zinc chloride in the presence of a water-soluble vitamin E. The presence of the water-soluble vitamin E acts to prevent the usual instability of hydrogen peroxide in a solution containing a metal salt while still allowing a desirable release of oxygen from the hydrogen peroxide when the mixture is used, that is, in the presence of organic matter.

Schaeffer (U.S. Pat. Nos. 4,687,663 and 4,849,213) discloses a dual-component system for delivering a first semi-solid component having hydrogen peroxide as an active ingredient and a second semi-solid component having sodium bicarbonate.

Ng, et al. (U.S. Pat. Nos. 4,788,052; 4,839,156; and 4,839,157) disclose stable hydrogen peroxide dental gel compositions including one having a combination of hydrophilic and hydrophobic fumed silicas along with a polyethylene glycol humectant, flavor, sweetening agent, sodium benzoate, and a nonionic surfactant as the essential ingredients. The order of addition of the essential ingredients is carefully controlled to protect the stability of the hydrogen peroxide.

From the foregoing, it is clear that numerous attempts have been made to safely utilize the therapeutic and bleaching capabilities of hydrogen peroxide As a liquid it can splash or otherwise be distributed as droplets which contact and damage other surfaces or tissue. Placed in a gel or semi-solid medium, the hydrogen peroxide reacts with most compounds to prematurely decompose and release its oxygen component thereby becoming water.

In view of the present state of the art it would be a significant advancement in the art to provide the dental professional with a high concentration of hydrogen peroxide in a safe, effective, and easily controllable vehicle for delivering the hydrogen peroxide to the dental surface being treated by the dental professional. It would also be an advancement in the art if the dental professional could have available hydrogen peroxide in an easily handled paste which would control the hydrogen peroxide and at the same time act as a polishing agent for polishing the dental surface. Such a novel invention is disclosed and claimed herein.

BRIEF SUMMARY AND OBJECTS OF THE INVENTION

This invention relates to a novel dental bleach system and method whereby the dental professional is provided with predetermined quantity of fumed silica and a premeasured volume of hydrogen peroxide solution which is mixed with the fumed silica immediately prior to application to the dental stain. The paste thus formed is easier to us and safer to handle with less risk to both the patient and the dental professional.

Both the fumed silica and the hydrogen peroxide are provided in a kit formed as a single patient use kit having a tray and a removable cover. The container for the fumed silica serves as a mixing chamber. The hydrogen peroxide solution is contained in an ampule that is also carried in a recess in the tray. A spatula is also provided to mix the hydrogen peroxide into the fumed silica to form a paste and then to apply the paste to the dental surfaces.

It is, therefore, a primary object of this invention to provide improvements in dental bleach systems.

Another primary object of this invention is to provide improvements in the method of removing stains from teeth.

Another object of this invention is to provide a single patient use kit wherein all of the required components for bleaching teeth are contained in the kit.

Another object of this invention is to provide a single patient use kit for bleaching teeth wherein a predetermined quantity of fumed silica is contained in a chamber in the kit, the chamber serving as a mixing chamber, and a premeasured volume of hydrogen peroxide solution is enclosed in an ampule.

These and other objects and features of the present invention will become more readily apparent from the following description in which preferred and other embodiments of the invention have been set forth in conjunction with the accompanying drawing and appended claims.

DETAILED DESCRIPTION OF THE PREFERRED EMBODIMENTS

Figure 1:
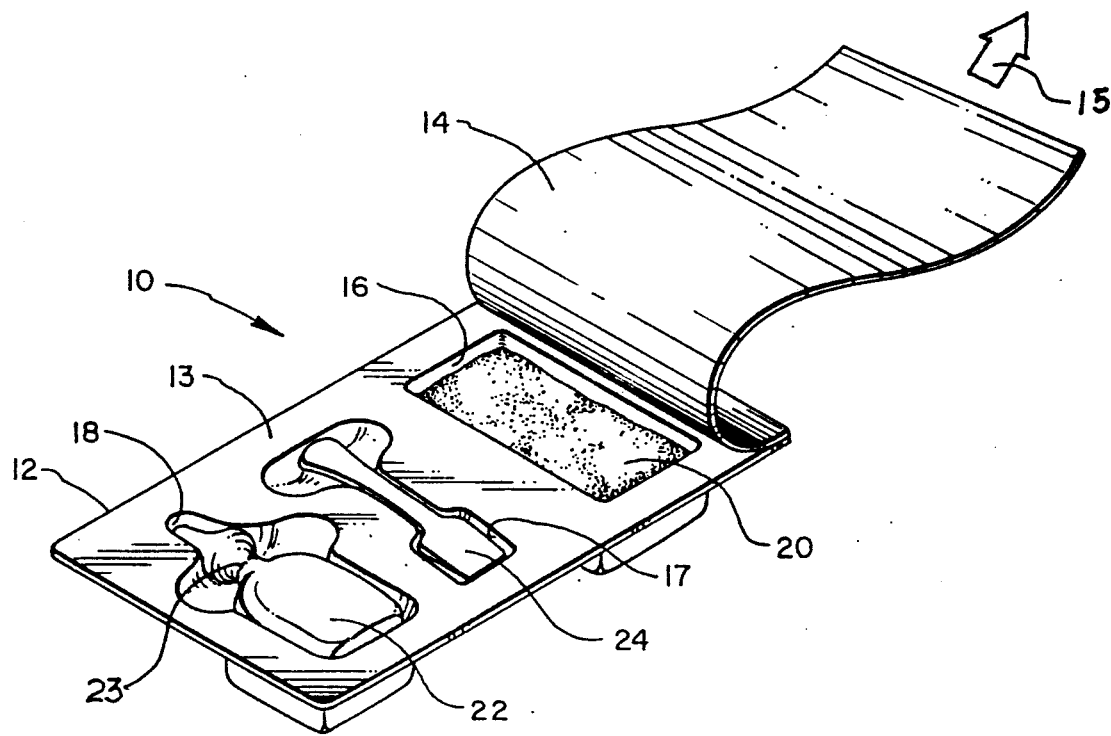
FIG. 1 is a perspective view of a first preferred embodiment of the novel dental bleach system of this invention shown as a single patient use kit.

The invention is best understood by reference to the drawing wherein like parts are designated by like numerals throughout in conjunction with the following description.

Referring now to FIG. 1, a presently preferred embodiment of a kit for presenting to the dental care professional the hydrogen peroxide solution and fumed silica in a safe, convenient manner is shown herein as a kit 10 having a tray 12 and a cover 14. Kit 10 is configured with a plurality of recesses 16-18 molded directly into the body of tray 12 so as to present a unitary design capable of holding a body of fumed silica 20 in recess 16, an ampule 22 in recess 18, and a spatula 24 in recess 17. Tray 12 is thermoformed from a sheet of plastic and includes a circumferential rim 13 against which cover 14 is releasably sealed. Trays similar to tray 12 are well known throughout the industry and are used in numerous applications not only for other dental applications but also for medical products, industrial products, consumer products, to name a few.

Ampule 22 is configured as a standard ampule having a frangible neck 23 whereby ampule 22 remains sealed until frangible neck 23 is broken at which time, the hydrogen peroxide solution in ampule 22 must be used within a reasonable period of time and can not be resealed. Ampule 22 is designed as a single patient quantity along with fumed silica 20 so that there is no tendency to use the contents of kit 10 for a second patient (not shown). This feature assures sterility in addition to product freshness for each patient being served by kit 10.

Cover 14 is releasably sealed to rim 13 of tray 12 and is fabricated from a suitable material such as a plastic, paper, or a nonwoven fibrous material. Cover 14 provides the necessary protection to the contents of tray 12; fumed silica 20, ampule 22, and spatula 24. If required, cover 14 can be any suitable material that will accommodate the appropriate sterilization of kit 10 either through gamma ray or ethylene oxide sterilization techniques. An important feature of cover 14 is that it is designed to be unidirectionally removable from tray 12 as shown schematically at arrow 15. This allows the user (not shown) to expose ampule 22 and spatula 24 prior to opening recess 16. This allows the user to obtain ampule 22 and break its frangible neck 23 prior to fumed silica 20 being exposed. This reduces the accidental scattering of fumed silica 20 by a puff of breath or the like.

Importantly, kit 10 is designed as a safe, convenient vehicle for providing the dental care professional with an easy to use, readily available, single patient use kit for bleaching the patient's teeth while, at the same time, supplying a source of hydrogen peroxide that is fresh and of a known concentration. Historically, the dental profession uses a commercially available hydrogen peroxide solution of 35% as a bleaching agent. (See, "The Role of Bleaching in Esthetics," *Dental Clinics of North America*, Vol. 33, No. 2, April 1989, pp 319-336, page 328.) I have found the range of 30% to 35% to be the most efficacious. Additionally, fumed silica 20 is provided as a premeasured volume in recess 16 which also serves as the mixing chamber for mixing the hydrogen peroxide solution in ampule 22 with fumed silica 20. This is an important advantage since it substantially eliminates spillage of hydrogen peroxide. Advantageously, the hydrogen peroxide solution is delivered as a unitary volume in ampule 22 versus being required to be poured from a larger container (not shown).

Fumed silica 20 is a very light, fluffy powder so that it also is more conveniently handled as a premeasured volume that is presented to the dental care professional in its own mixing chamber, recess 16. Fumed silica is notorious for its tendency to be easily scattered even upon a slight puff of breath. Accordingly, kit 10 is prepared in such a manner as to provide access to ampule 22 of hydrogen peroxide solution before exposing fumed silica 20. The operator (not shown) is able to open ampule 22 before pulling cover 14 open further to expose fumed silica 20. With fumed silica 20 exposed, the operator (not shown) mixes the hydrogen peroxide solution from ampule 22 directly therein using spatula 24 to thoroughly blend the hydrogen peroxide solution with fumed silica 20. The paste-like material 21 (FIG. 2) is conveniently held in recess 16 until used according to the practice of this invention.

Figure 2:
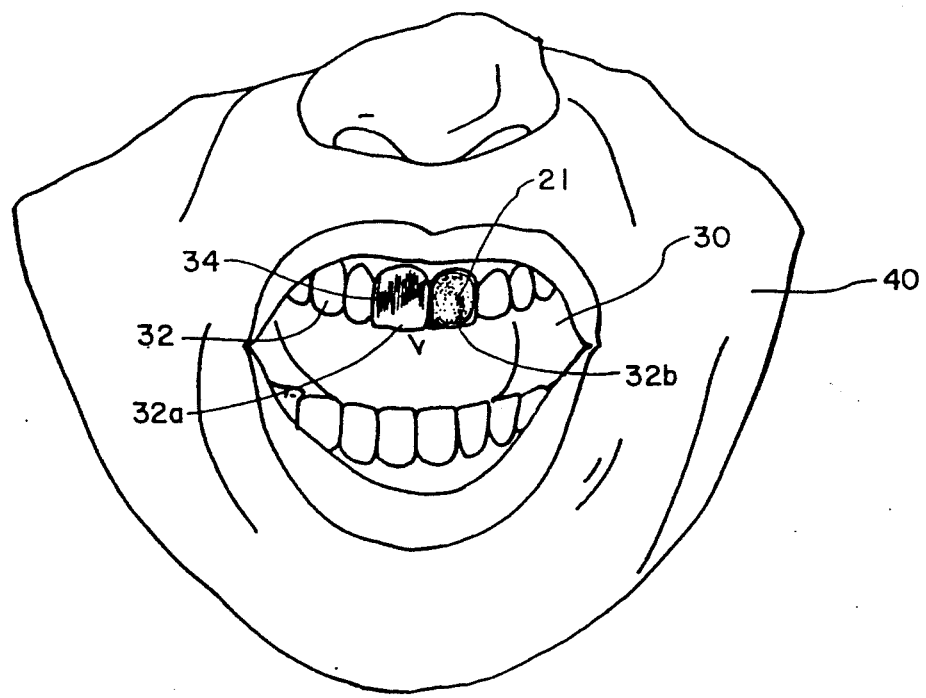
FIG. 2 is a frontal view of a person's teeth with the dental bleach composition prepared from the kit of FIG. 1 placed on one of the teeth, the person's mouth and teeth being shown to illustrate the environment of the invention.

Referring now more particularly to FIG. 2, paste 21 is shown applied to a tooth 32b of a set of teeth 32 in the mouth 30 of a patient 40 (illustrated schematically to show the environment of usage of paste 21). A second tooth, tooth 32A includes a stain 34, a similar stain on tooth 32b being covered by paste 21. Advantageously, paste 21 is conveniently and safely applied to teeth 32 since it is a paste with a semi-solid consistency and does not flow, drip, or otherwise spread away from the area of its placement. This is particularly important since a 35% solution of hydrogen peroxide is quite caustic to tissue such that it will cause chemical burns on such tissue unless properly controlled. Clearly, of course, the ordinary dental practices such as the use of a rubber dam are followed.

THE METHOD

In practicing the novel method of this invention, the dental professional (not shown) carefully prepares patient 40 according to the practices of the profession. This may include, for example, cleaning teeth 32 and isolating teeth 32a and 32b with a conventional rubber dam (not shown). Thereafter, when ready to proceed with the bleaching process the dental professional obtains kit 10 and carefully removes cover 14 as indicated by arrow 15 only to the extent of exposing ampule 22 and spatula 20. Fumed silica 20 is temporarily kept covered by cover 14 until the dental professional is ready to produce the bleaching paste. Ampule 22 is then retrieved along with spatula 24. Cover 14 is pulled away from recess 16 as shown by arrow 15 to expose fumed silica. Frangible neck 23 is broken and the hydrogen peroxide solution in ampule 22 is poured into fumed silica 20 while mixing with spatula 24 until a paste 21 of hydrogen peroxide solution and fumed silica 20 has been formed.

Paste 21 is carefully applied to teeth 32 using spatula 24 to dip paste 21 from recess 16 and apply it to teeth 32. Paste 21 is left on teeth 32 for a physiologically suitable period of time to achieve bleaching effect on stain 34 after which paste 21 is removed from teeth 32. Additional applications of paste 21 may be made to teeth 32 as determined by the dental professional (not shown).

It is extremely important to emphasize that the novel system and method of this invention is for use strictly by a dental professional. The concentration of hydrogen peroxide (30% to 35%) in the hydrogen peroxide solution renders its use dangerous in the hands of a lay person or any other person unskilled in handling such a powerful bleaching solution.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A dental bleach system for use by a dental professional to bleach teeth comprising:
   a kit comprising a tray having at least a first compartment and a second compartment, said first compartment containing a sealed container of hydrogen peroxide solution having a concentration of hydrogen peroxide substantially within the range of 30% to 35% by volume, said second compartment comprising a mixing chamber and containing a body of fumed silica, said hydrogen peroxide solution and said body of fumed silica comprising a single patient application;
   mixing means for mixing said hydrogen peroxide solution with said fumed silica in said mixing chamber to produce a paste of said hydrogen peroxide solution and said fumed silica;
   application means for applying said paste to the teeth for a predetermined period of time for bleaching the teeth; and
   a cover releasably sealed to said tray, said cover being removable to expose said first compartment before said second compartment to allow the dental professional to retrieve said sealed container of hydrogen peroxide solution prior to exposing said body of fumed silica.

2. The dental bleach system defined in claim 1 wherein said sealed container comprises an ampule having a frangible neck for providing a one time access to said hydrogen peroxide solution.

3. The dental bleach system defined in claim 1 wherein said mixing means comprises a spatula and said tray comprises a third compartment for receiving said spatula, said spatula serving as said mixing means and as said application means for applying said paste to the teeth.

4. A dental bleach system for use by a dental professional for bleaching teeth comprising:
   a tray, said tray comprising a first compartment, a second compartment, and a cover removably mounted to said tray to enclose said first compartment and said second compartment, removal of said cover exposing said first compartment before said second compartment;
   an ampule containing a quantity of hydrogen peroxide in said first compartment, said quantity of hydrogen peroxide having a concentration of hydrogen peroxide substantially within the range of 30% to 35% by volume;
   a body of fumed silica in said second compartment;
   mixing means for mixing said hydrogen peroxide into said fumed silica in said second compartment to form a paste comprising said fumed silica and said quantity of hydrogen peroxide, said paste being prepared immediately prior to being applied to the teeth and
   application means for applying said paste to the teeth.

5. The dental bleach system defined in claim 4 wherein said ampule contains a single patient quantity of said hydrogen peroxide.

6. The dental bleach system defined in claim 4 wherein said second compartment comprises a container for said fumed silica, said container holding a body of said fumed silica sufficient for a single patient application.

7. The dental bleach system defined in claim 4 wherein said mixing means comprises a spatula means for blending said hydrogen peroxide with said fumed silica.

8. The dental bleach system defined in claim 7 wherein said application means comprises said spatula means.

9. A method for bleaching teeth by a dental professional comprising:
   obtaining a body of fumed silica;
   preparing a solution of hydrogen peroxide, said hydrogen peroxide being present in said solution at a concentration substantially within the range of 30% to 35% by volume;
   sealingly enclosing said solution of hydrogen peroxide in a single patient use ampule;
   selecting a tray with a mixing chamber and packaging said ampule in said tray adjacent said mixing chamber;
   releasably sealing said tray with a cover, said cover being selectively removable to expose said hydrogen peroxide prior to exposing said fumed silica;
   forming a bleaching paste by mixing said solution of hydrogen peroxide with said fumed silica in said mixing chamber; and
   applying said bleaching paste to the teeth.

10. The method defined in claim 9 wherein said obtaining step includes providing said body of fumed silica as a single patient quantity of fumed silica and sealingly enclosing said body of fumed silica in said mixing chamber.

11. The method defined in claim 9 wherein said forming step includes mixing said solution with said fumed silica in said mixing chamber.

12. The method defined in claim 9 wherein said applying step comprises depositing a predetermined quantity of said bleaching paste to the teeth for a physiologically acceptable period of time to allow said hydrogen peroxide to bleach the teeth.

* * * * *